United States Patent [19]

Halling et al.

[11] Patent Number: 5,407,808
[45] Date of Patent: Apr. 18, 1995

[54] METHOD AND COMPOSITION FOR PHOTODYNAMIC TREATMENT AND DETECTION OF TUMORS

[75] Inventors: Blaik P. Halling, Yardley, Pa.; Debra A. Yuhas, Parlin, N.J.

[73] Assignee: FMC Corporation, Philadelphia, Pa.

[21] Appl. No.: 170,467

[22] Filed: Dec. 20, 1993

Related U.S. Application Data

[60] Division of Ser. No. 814,305, Dec. 23, 1991, Pat. No. 5,298,502, which is a continuation-in-part of Ser. No. 622,303, Dec. 5, 1990, abandoned, which is a continuation-in-part of Ser. No. 535,076, Jun. 8, 1990, abandoned, which is a continuation-in-part of Ser. No. 351,331, May 3, 1989, abandoned, which is a continuation-in-part of Ser. No. 335,007, Apr. 7, 1989, abandoned, which is a continuation-in-part of Ser. No. 285,151, Dec. 12, 1988, abandoned.

[51] Int. Cl.$^6$ .......................... C12Q 1/04; C12Q 1/26; G01N 33/48; A61K 31/40

[52] U.S. Cl. ............................ 435/34; 435/25; 435/189; 424/7.1; 424/9; 436/63; 436/64; 436/813; 514/410

[58] Field of Search ............. 435/25, 34, 189; 424/7.1, 9; 436/63, 64, 813; 514/410

[56] References Cited

U.S. PATENT DOCUMENTS

| | | | |
|---|---|---|---|
| 4,977,177 | 12/1990 | Bommer et al. | 514/410 |
| 5,002,962 | 3/1991 | Pandey et al. | 514/410 |
| 5,053,423 | 10/1991 | Liu | 514/410 |

OTHER PUBLICATIONS

El-Far et al. "Selective in Vivo Tumor Localization of Uroporphyrin Isomer I in Mouse Mammary Carcinoma: Superiority over Other Porphyrins in a Comparative Study" Cancer Res 46:4390-4394 1986.

Mang et al. "Fluorescence Detection of Tumors" Cancer 71(1):269-276 1993.

Goff et al. "Effects of Photodynamic Therapy with Topical Application of 5-Aminolevulinic acid on normal skin of hairless guinea pigs" J Photochem Photobiol B:Biol 15:239-251 1992.

Camadro et al. "Kinetic Properties of Membrane Bound Human Liver Mirochondrial Protoprophyrinogen Oxidase" Arch Biochem Biophys 242(1):206-212 1985.

H. A. Dailey et al., "Bovine Ferrochelatase", J. Biol. Chem., vol. 258, pp. 11453-11456 (1983).

*Primary Examiner*—Michael G. Wityshyn
*Assistant Examiner*—Nancy J. Gromet
*Attorney, Agent, or Firm*—Robert M. Kennedy; Norman L. Craig; Abner Sheffer

[57] ABSTRACT

Disclosed is a method and a pharmaceutical composition for killing mammalian tumor cells by subjecting the cells to light in the presence of a light-activatable tetrapyrrole, in which the improvement comprises treating the cells with a compound which inhibits the enzymatic conversion of protoporphyrinogen to protoporphyrin IX by protoporphyrinogen oxidase in the cells thereby causing a buildup of protoporphyrin IX in the cells. Also disclosed is a method for the production of protoporphyrin IX which comprises growing eukaryotic microalgae in the presence of a protoporphyrinogen oxidase inhibitor.

21 Claims, 1 Drawing Sheet

METHOD AND COMPOSITION FOR PHOTODYNAMIC TREATMENT AND DETECTION OF TUMORS

This application is a division of application Ser. No. 814,305, filed Dec. 23, 1991, now U.S. Pat. No. 5,298,502, which is a continuation-in-part of application Ser. No. 622,303, filed Dec. 5, 1990, abandoned, which is a continuation-in-part of application Ser. No. 535,076, filed Jun. 8, 1990, abandoned, which is a continuation-in-part of application Ser. No. 351,331, filed May 3, 1989, abandoned, which is a continuation-in-part of application Ser. No. 335,007, filed Apr. 7, 1989, abandoned, which is a continuation-in-part of application Ser. No. 285,151, filed Dec. 12, 1988, abandoned.

One aspect of this invention relates to the photodynamic treatment of mammalian tumor cells, as in the photodynamic treatment of cancer.

It is by now well known to supply hematoporphyrin derivative or a mixture of porphyrins derived therefrom (e.g. Photofrin II,) to mammalian tumor cells and then subject such cells to light of appropriate wavelength to effect cell destruction. Such photodynamic therapy is the subject of a series of articles making up a special issue of *Photochemistry and Photobiology*, Volume 46, number 5, November, 1987 (hereinafter "P&P 46-5"). As shown in those articles, such photodynamic therapy has been used in the treatment of a wide variety of cancers (including such solid tumors as cancers of the bronchial tubes, bladder, esophagus, lung, skin, head and neck, brain, and colon and intraocular and gynecologic cancers). It has been stated that the biochemical effects of such porphyrin photosensitization include the cross-linking of membrane proteins, the peroxidation of lipids, the inhibition of transport of some essential metabolites, the lysis of lysosomal and mitochondrial membranes, the inactivation of several enzymes and an increased cell uptake of porphyrins (P&P 46-5, page 695). The porphyrin material is generally injected (e.g. intravenously or intraperitoneally), a typical dose being about 2 mg of Photofrin II per kg of body weight.

The porphyrin material may also be incorporated into a liposome and injected (e.g. intraperitoneally), as disclosed for instance in Spikes et al., "Photodynamic Behavior of Porphyrins in Model Cell, Tissue and Tumor Systems"; in *Photodynamic Therapy of Tumors and Other Diseases* (Edited by G. Jori and C. A. Perria); pages 45-53; Libreria Progetto, Padua (1985), and references cited therein.

The technical literature indicates that the introduction of protoporphyrin into cells, such as human erythrocytes (Dubbelman et al, Biochimica et Biophysica Acta, 511 (1978) 141-151) or murine leukemia cells (Kessel, Cancer Research 42, 1703-1706 May 1982), has a marked photosensitizing effect. The Kessel article states that it was the most potent photosensitizing agent of those tested. However, when Kessel and others (e.g. Berenbaum et al, Br. J. Cancer (1982) 45, 571-581)injected protoporphyrin into animals they found no detectable protoporphyrin in the tumors, indicating that protoporphyrin introduced as such into the body may be readily lost into the circulation.

It is also well known to employ hematoporphyrin derivative and similar materials for the detection and localization of tumors, such as cancer of the bladder or lungs (P&P 46-5, page 759, for instance).

In one aspect of this invention the agent for treating the cells in such photodynamic treatment, or in the known methods for detection and localization of tumors, (as in the detection and definition of tumor margins of skin cancers) is not a porphyrin, or is not solely a porphyrin. Instead it comprises an enzyme-inhibitor agent which inhibits the enzymatic conversion of protoporphyrinogen to heme in said cells, thereby causing a buildup of endogeneous protoporphyrin IX in said cells. We have ascertained that agents, such as certain types of herbicidal compounds, which inhibit the enzymatic conversion of protoporphyrinogen to chlorophyll in plant cells also inhibit the enzymatic conversion of protoporphyrinogen to heme in mammalian cells. We believe that the inhibition by such agents probably affects the step of conversion of protoporphyrinogen to protoporphyrin IX by an enzyme (protoporphyrinogen oxidase, EC 1.3.3.4), so that the protoporphyrinogen cannot follow the normal enzymatic pathway to protoporphyrin IX but instead becomes oxidized in the cell (e.g. in the plasma) but outside the normal enzymatic pathway (e.g. outside the organelle membrane), and that the result is an accumulation of protoporphyrin IX in locations where it is unavailable for the normal conversion to heme, with the result that, when the cells are subjected to light, this accumulated protoporphyrin IX has a cell-destroying effect like that exhibited in the above-described photodynamic treatment.

The enzyme-inhibiting agents of this invention are specific inhibitors of the enzymatic conversion of protoporphyrinogen to heme in the sense that they do not operate as general enzyme poisons such as denaturing or cross-linking agents (e.g. sulfhydryl reagents), preferably they are not materials which affect the oxidation conditions such as electron acceptors; thus, preferred agents for this invention have redox potentials more negative than about $-500$ mV, such as more negative than $-800$ mV (measured, for instance in conventional manner in an aprotic solvent for the agent, as by cyclic voltametry or polarographically). It is also preferred that the agent not be a tetrapyrrole and that its $I_{50}$ for protoporphyrinogen oxidase be less than about 10 $\mu$M (a $pI_{50}$ greater than about 5), more preferably less than about 1 $\mu$M (a $pI_{50}$ greater than about 6) such as less than about 0.3 $\mu$M, e.g. an $I_{50}$ of about 0.1 or 0.03 or 0.01 $\mu$M or less.

Figure 1:
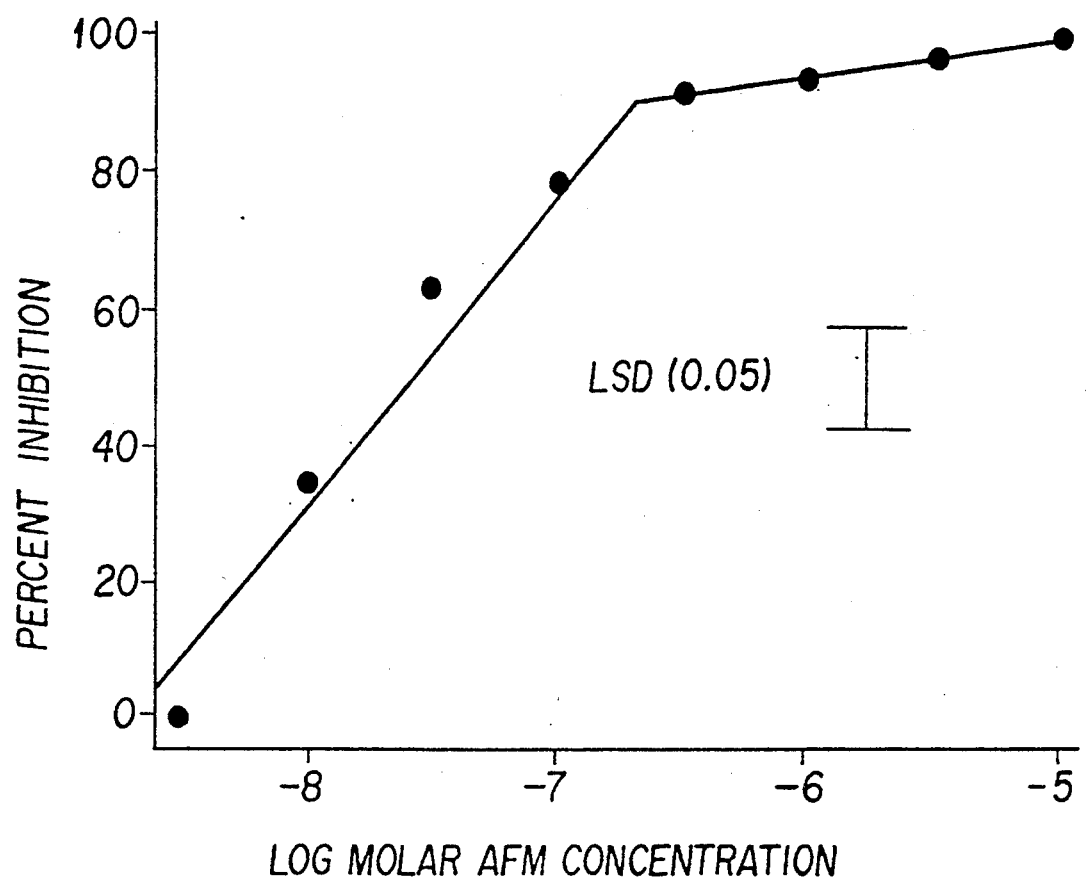
FIG. 1 is a graph of percent inhibition vs. log molar concentration of inhibitor, from which the $I_{50}$ value (the concentration which provides 50% inhibition) can be determined.

The enzyme-inhibiting agent is preferably one which has a high capacity for disrupting the plasmalemma of plant material. One test for that capacity is the Efflux Experiment described in the article by Halling and Peters in *Plant Physiology*, 84, 1114-5 (1987). In such a test (described in more detail in Appendix A below), preferred agents show a total efflux of at least 50% at a treatment rate of 100 $\mu$M, preferably at a treatment rate of 1 $\mu$M or less, such as 100 nM; highly active materials, such as 1-(4-chloro-2-fluoro-5-propargyloxyphenyl)-3-methyl-4-difluoromethyl-$\Delta^2$-1,2,4-triazolin-5-one or lactophen (described below), give total efflux percentages of over 90% at 100 nM concentration.

Another test of the capacity of a material for disrupting the plasmalemma of plant material is the Light-Induced Greening Inhibition Test described more particularly in Appendix B below. This test measures the capacity to inhibit the light-greening of dark-bleached *Chlamydomonas reinhardi* mutant y-1 (a type of algae which when grown in the dark does not make chlorophyll, so that the mass of algae becomes bleached owing to the presence of new non-green cells, and which produces chlorophyll again when it is exposed to light). Many of the preferred compounds (agents) used in this invention have the ability to inhibit the light-greening by at least 50% when the compound is used at a concentration of $10^{-5}M$, more preferably at a concentration of $10^{-6}M$ or less, e.g. $10^{-7}M$. However, compounds which are ionized in water, such as compounds like 6c (of Example 6 below) in which the operative ion is negatively charged do not respond well in this test; apparently the algal cells resist entry of the acidic group. In addition, many of the preferred compounds, when used at said concentration in the Light-Greening Inhibition Test, give a supernatant which shows a light absorption peak at about 405 nm which is higher than the chlorophyll peak (the peak at about 668 nm in this system), e.g. the supernatant shows a 405 nm peak whose height is 2, 3 or 4 times the height of the 668 nm peak.

Among the enzyme-inhibiting agents which may be employed in the practice of this invention are herbicidal compounds of the following classes (A to G):

A. Aryl heterocyclic herbicides of the general formula

Ph—NHet where "Ph" is a substituted phenyl, preferably 2,4-disubstituted phenyl, more preferably a 2,4,5-trisubstituted phenyl, and NHet is a 5- or 6-membered heterocyclic ring having one to four ring-nitrogen atoms and having the formula

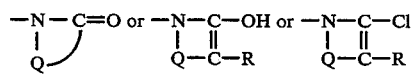

where Q represents the balance of the heterocyclic ring and R represents hydrogen or a substituent group. This class of compounds includes such materials as those designated as "the cyclic imide class of herbicides" in an article by Wakabayashi et al., *J. Pesticide Sci.* 11, 635-460 (1986) which shows the following compounds in its FIG. 1:

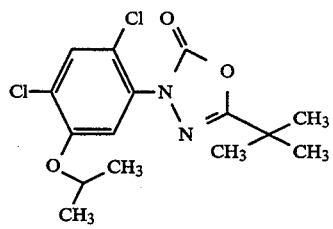

I

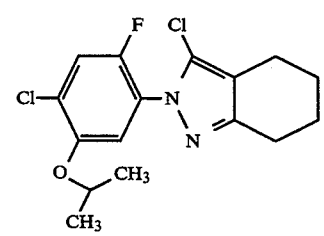

II

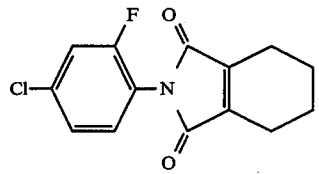

III

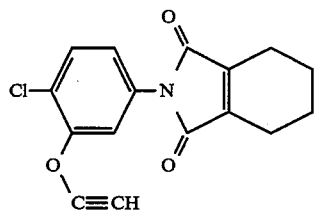

IV

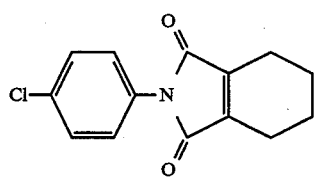

V

Compound I is an aryl oxadiazole herbicide, namely 2-tert-butyl-4-(2,4-dichloro-5-isopropoxyphenyl)-$\Delta^2$-1,3,4-oxadiazolin-5-one. Other 2-alkyl-4-(2,4,5-trisubstituted phenyl)-$\Delta^2$-1,3,4-oxadiazolin-5-ones which may be used in the present invention are disclosed, for instance, in U.S. Pat. Nos. 3,385,862; 3,836,539; and 3,876,413.

Compound II is an aryl tetrahydroindazole herbicide, namely 3-chloro-2-(4-chloro-2-fluoro-5-isopropoxyphenyl)-4,5,6,7-tetrahydro-2H-indazole. Other 3-substituted-2-(2,4,5-trisubstituted phenyl)tetrahydro indazoles which may be used in the present invention are disclosed, for instance, in U.S. Pat. No. 4,670,043.

Compounds III, IV and V are aryl tetrahydrophthalimide herbicides. Other aryl tetrahydrophthalimides which may be employed in the present invention are disclosed, for instance, in U.S. Pat. Nos. 4,431,822; 4,670,046; 4,670,042; and 4,439,229 and published International application (PCT) WO 87/07602. The latter two citations above also disclose other NHet rings which may be used, such rings being illustrated, for example, at column 4 line 25 to column 5 line 20 of U.S. Pat. No. 4,439,229 and at pages 12 to 14 of WO 87/07602.

Other suitable herbicides of the PH-NHet type are:
aryl triazolinones, such as those disclosed in U.S. Pat. Nos. 4,318,731; 4,398,943; 4,404,019; 4,702,945; 4,705,557; 4,702,763; 4,761,174 and International applications (PCT) WO 85/01637, WO 85/04307, WO 87/00730, WO 87/03782, WO 86/04481, and WO 88/01133;

aryl tetrazolinones, such as those disclosed in U.S. Pat. No. 4,734,124 and International applications (PCT) WO 85/01939 and WO 87/03873;

aryl triazinediones, such as those disclosed in U.S. Pat. Nos. 4,755,217 and 4,766,233 and International application (PCT) WO 86/00072;

aryl hydantoins, such as those disclosed in U.S. Pat. No. 4,427,438;

aryl imidazolopyrimidines, such as those disclosed in West German patent DT 2604989 (Derwent Abstracts accession No. 65326X), Japanese Kokai J60-158147A (Derwent Abstracts accession No. 85-240363), and European published patent application EP 230874 (Derwent Abstracts accession No. 87-215141);

aryl pyridyldiazines, such as compounds of the type of compound 8x of Example 8 below;

aryl diazinediones, such as compounds of the type of compounds 8e and 8v of Example 8 below;

aryl pyradiazinones, such as compounds of the type of compound 8f of Example 8 below;

aryl oxadiazolinones, such as those disclosed in Japanese Kokai J59-148769 (Derwent Abstracts accession No. 84-246947) or Japanese Kokai J62-161772 (Derwent Abstracts accession No. 87-238787);

aryl oxadiazinones, such as compounds of the type of compounds 8k and 8m of Example 8 below;

aryl benzamidazoles, such as compounds of the type of compound 8ad of Example 8 below;

aryl iminotriazolopyridazines, such as those disclosed in U.S. Pat. Nos. 4,913,723; 4,906,281; and 4,906,279;

aryl thiazoles, such as compounds of the type of compounds 8L, 8r and 8ah of Example 8 below;

aryl pyrroles, such as those disclosed in European published patent applications EP 255601 (Derwent Abstracts accession No. 88-037583) and EP 260288 (Derwent Abstracts accession No. 88-127433);

aryl urazoles, such as those disclosed in U.S Pat. No. 4,452,981; and aryl hexahydropyridazines, such as those disclosed in U.S. Pat. No. 4,619,687.

B. Aryl heterocyclic urethanes, such as those disclosed in U.S. Pat. No. 4,521,242.

C. Aryl heterocyclic ureas, such as those disclosed in Japanese Kokai J58-225081 (Derwent Abstracts Accession No. 84-034261).

D. Aryl amides, such as compounds of the type of compounds 8aj and 8ak of Example 8 below.

E. Phenyl ether herbicides, such as those having a p-halo or p-nitro phenoxyphenyl structure, such as the following commercially available materials:

5-(2-chloro-4-(trifluoromethyl)phenoxy)-2-nitro-N-methanesulfonylbenzamide (fomesafen)

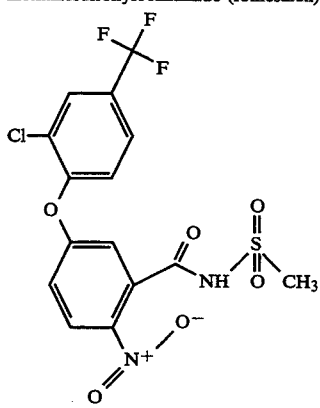

methyl 5-(2,4-dichlorophenoxy)-2-nitrobenzoate (bifenox)

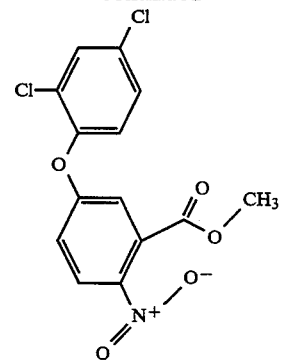

sodium 5-(2-chloro-4-(trifluoro-methyl)phenoxy)-2-nitrobenzoate (acifluorfen)

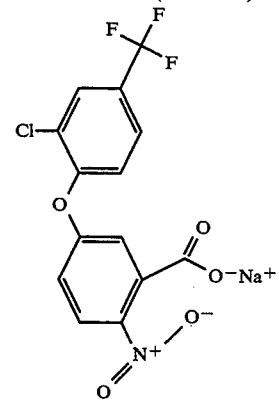

2-chloro-1-(3-ethoxy-4-nitro-phenoxy)-4-trifluoromethylbenzene (oxyfluorfen)

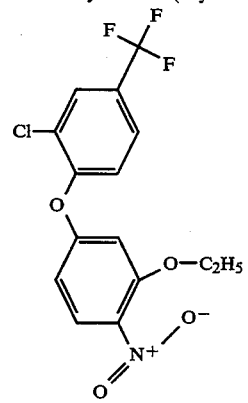

Other suitable commercially available diphenyl ether herbicides are lactophen: 1-(carboethoxy)ethyl 5-(2-chloro-4-trifluoromethylphenoxy)-2-nitrobenzoate, fluoroglycofen: (carboethoxy)methyl 5-(2-chloro-4-trifluoromethyl-phenoxy)-2-nitrobenzoate, chloronitrofen: 2,4,6-trichloro-(4-nitrophenoxy)-benzene, fluorodifen: 2-nitro-1-(4-nitrophenoxy)-4-trifluoromethylbenzene, nitrofen: 2,4-dichloror-1-(4-nitrophenoxy)benzene, chlomethoxyfen: 4-(2,4-dichlorophenoxy)-2-methoxy-1-nitrobenzen.

Still another suitable diphenyl ether herbicide is methyl 5-(2-chloro-4-trifluoromethylphenoxy)-2-nitroacetophenone oxime-O-acetate.

F. Aryl pyrazole herbicides such as those disclosed in U.S. Pat. Nos. 4,563,210; 4,496,390; and 4,459,150 and German Offenlegungsschrift 3520327 A1.

G. Compounds of the formula

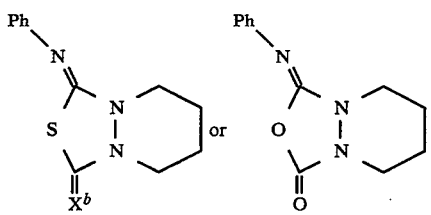

where $X^b$ is O or S and "Ph" has the meaning described above, such as compounds disclosed in European published patent application EP 273417 or Derwent Abstracts accession no. 87-040749.

Some enzyme-inhibiting herbicides are disclosed in Matringe et al., *FEBS Letters*, Vol. 245, no. 1,2, pages 35–38 (1989) and Yanase et al., *Pesticide Biochemistry and Physiology*, Vol. 35, pages 70–80 (1989).

Treatment with the agents of this invention may be effected by intravenous or intraperitoneal injection. The agent may be used as a sterile composition comprising the agent dissolved or dispersed in a pharmaceutically acceptable carrier, for example as an aqueous isotonic solution such as aqueous saline (e.g. 0.9% NaCl) or Dulbecco's phosphate buffered saline (PBS) at a concentration of, say, 2.5 mg mL$^{-1}$, or comprising the agent in a liposomal system such as one prepared with a phospholipid vesicle in a manner such as described at pages 1659–1660 of *Remington's Pharmaceutical Sciences*, 1985, (17th edition), published by Mack Publishing Company. For instance, analogously to the formulation described by Jori et al., *Br. J. Cancer* (1983), 48 at page 307, 51.4 mg. of dipalmitoyl-diphosphatidyl-choline may be dissolved in 10 mL of a 1 mM solution of the agent in chloroform-methanol (9:1, v/v), and after thorough mixing the solvent may be removed under vacuum at 30° C., giving a solid which may be resuspended in 10 mL of 0.01M phosphate buffer at pH 7.4 containing 150 mM NaCl, and the cloudy solution then sonicated for 30 minutes at 50° C. For this purpose multilamellar liposomes of POPC (1-palmitoyl-2-oleyl-sn-glycero-3-phosphocholine) may also be used.

The enzyme-inhibiting agents which may be employed in the practice of this invention may be conjugated or linked to appropriate tumor-specific monoclonal antibodies (MABs), using linker technology known in the art, as a means for targeting the enzyme-inhibiting agent to particular tumor sites.

The enzyme-inhibiting agents used in this invention may also be used by simple oral ingestion, preferably in diluted form together with a pharmaceutically acceptable carrier, as by adding them to food as illustrated in Example 6 below.

It may be desirable, especially for oral administration, to employ enzyme-inhibiting agents which are water-soluble salts or which are acidic and form water-soluble sodium or potassium salts, such as an acidic sulfonamide of the type disclosed in International applications (PCT) WO 87/03782 (e.g. agent 6c in Example 6 below) or WO 85/001939 and WO 87/037873 or a water-soluble salt thereof, or a carboxylic acid or water-soluble salt thereof such as the sodium salt known as acifluorfen.

The enzyme-inhibiting agents which may be used in this invention may be incorporated into conventional pharmaceutical preparations such as tablets (e.g. compressed tablets which may be coated, as with sugar paste and/or syrup), suppositories, capsules (e.g. hard gelatine capsules), suspensions, solutions, powders or ampules. In such preparations the agent may be present in admixture with a pharmacologically acceptable solid and/or liquid carrier which may, if desired, be a nutrient; for example it may be a solid such as corn starch or a liquid diluent, such as water or an edible oil or mineral oil or a solvent e.g. dimethyl sulfoxide. Mixtures of the enzyme-inhibiting agents may be used, e.g. a mixture of agent 6c of Example 6 below and acifluorfen in, for instance, approximately equal proportions. The dosage to be employed may be determined by routine experimentation, well known in the art, such as experiments of the type described, for Photofrin II, in the article by Dougherty on "Photodynamic Therapy (PDT) of Malignant Tumors" in CRC Critical Reviews in Oncology/Hematology vol. 2, issue 2 (1984), pages 83–116.

The agent may be administered in combination with a drug (such as verapamil, cyclosporine, or quinine) known to increase the sensitivity of resistant cancer cells to anticancer drugs.

The agent may be administered in combination with 5-aminolevulinic acid (ALA), a material which is known to selectively induce phototoxic concentrations of protoporphyrin IX in various malignant tumors. Some methods of administration are by injection (e.g. an intraperitoneal injection of a solution containing, say, about 10–250 mg of ALA per kilogram of body weight); by ingestion (e.g. at a dosage of about 20–500 mg of ALA per kilogram of body weight per day); or topically to the skin (e.g. in a water-based moisturizing cream containing about 20–50% of ALA) or to internal organs (as in a spray of an aqueous solution of the ALA). The enzyme-inhibiting agent may be administered in admixture with the ALA by such methods, or it may be administered separately, preferably prior to (e.g. for one or more days prior to) the administration of the ALA. In tests with suspensions of hela cells it has been found, for instance, that supplying the agent to the culture medium (e.g. in 10 or 100 $\mu$M concentration of the agent) 24 hours before the addition of the ALA to the culture medium increased the amount of porphyrin produced; the agent apparently served to set up a block in the mitochondrial pathway to protoporphyrin IX prior to stimulation of porphyrin synthesis with ALA. Topical applications may be used, for instance, for treatment of actinic keratoses, primary basal cell and squamous cell carcinomas, and transdermal secondaries of breast carcinoma. As in the case of treatment with the enzyme-inhibiting agent alone, the tumor-destroying treatment with light is preceded by a period during which protoporphyrin IX accumulates in the tumor; this accumulation can be seen, in many cases, by the fluorescence of the tumor under UV light (e.g. at 340 nm).

Porphyrins have been employed for the photodynamic therapy of skin lesions, such as papilloma viral lesions, wads, psoriasis vulgaris, and hypervascular dermal lesions such as "port-wine stains" and "spider veins". The enzyme-inhibiting agents described herein may also be employed in such photodynamic therapy, being administered in the ways described above or by topical application or intracutaneous or intralesional injection. For topical application they may be mixed with enhancers of percutaneous penetration such as Azone (1-dodecylazacycloheptan-2-one) or Pharmasolve (which contains alcohol, propylene glycol, polyoxyethylene lauryl ether, dioctylsodium sulfosuccinate and water; see published European patent application EP 350,036). Here again the agent may be administered in admixture with ALA.

The following Examples are given to illustrate this invention further.

EXAMPLE 1

HeLa cells (a human tumor cell line commonly employed for tumor research and obtained from the American Type Culture Collection), in logarithmic growth phase (having been cultured at 37° C. for five days in one-liter Falcon tissue culture flasks), were washed in phosphate buffered saline (PBS). A 0.25% solution of trypsin in PBS (2 mL) was added, and, after several minutes, the cells were gently removed from the flask and placed into 110 mL of a 25 mM solution of Hepes in Minimum Essential Medium (MEM) supplemented with 10% v/v inactivated calf serum, 1.1 mL of a 200 mM solution of glutamine in 0.85% saline solution, and 11,000 units of penicillin/11,000 mcg streptomycin.

Then, 5.0 mL aliquots of the resulting resuspended cell culture were each placed into a 50 mL Falcon tissue culture flask and (except for the control) mixed with the treating agent. The aliquots were then incubated in the dark at 37° C. for three days. The cells were then removed and extracted under green light in the following manner:

Cells were removed from the bottom of the flask with the addition of 0.8 mL of a 0.25% solution of trypsin in PBS. After 1 hour of incubation in the dark, cells and medium were removed from the flasks, placed into round bottom centrifuge tubes, and then subjected to two rounds of freeze-thaw conditions to disrupt the cells and allow for extraction.

Examination of cell suspensions after this disruption regime revealed no intact cells. Ten mL of basic acetone (90% acetone:10% of 0.1N NH$_4$OH) was then added to each tube, and the tubes were centrifuged to remove protein and cell debris. Five mL of water was added to the supernatant, followed by 0.5 mL of a saturated aqueous solution of NaCl. The pH was then adjusted to 6.8 by the dropwise addition of 2M KH$_2$PO$_4$. The aqueous acetone extract was then loaded onto a C8 Baker Prep column. The columns were dried and then washed with 2 mL of water. The tetrapyrroles were eluted with 2×1.5 mL volumes of 90/10 CH$_3$OH/H$_2$O. Extracts were then quantified on a spectrofluorometer.

The treating agents used in this experiment were:
A. 5-amino levulinic acid, which is a known precursor of tetrapyrroles.
B. Acifluorfen-methyl having the formula:

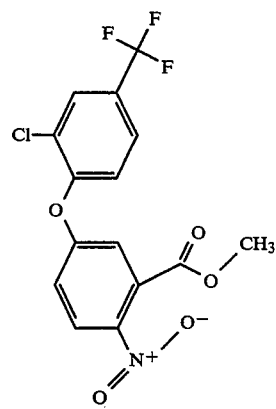

C. A herbicide of the formula:

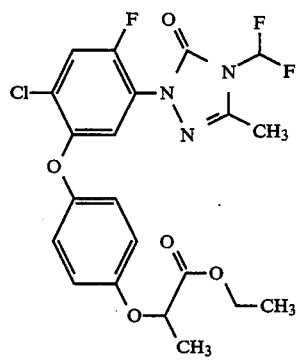

D. A herbicide of the formula:

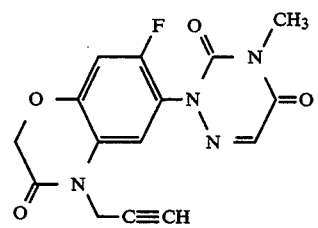

E. A herbicide of the formula:

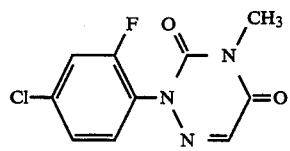

Agent A was supplied as a filter-sterilized 250 mM solution in water, pH 6.5. Agents B, C, D, and E were supplied as 50 mM solutions in acetone. Acetone was also added to the control to provide a concentration of 0.2% v/v therein. The amounts of the agents added to the cell cultures were such as to give the concentrations specified in the Table 1 below. The amounts of the tetrapyrrole protoporphyrin IX ("Proto IX") produced are shown in that Table.

TABLE 1

Tetrapyrrole accumulation in treated HeLa cells

| Agent | Concentration of Agent [μM] | Fluorescence Emission cps 400/630 | Amount of Proto IX (pmoles) |
| --- | --- | --- | --- |
| A | 5000 | 41842 | 4.2 |
| B | 100 | 12921 | 1.3 |
| C | 100 | 33477 | 3.5 |
| D | 100 | 10551 | 1.1 |
| E | 100 | 8967 | 0.9 |
| control |  | 2795 | 0.3 |

EXAMPLE 2

HeLa cells, in logarithmic growth phase having been cultured for 6 days in six one-liter Falcon tissue culture flasks at 37° C.), were washed in phosphate buffered saline (PBS). A 0.25% solution of trypsin in PBS was added, and, after several minutes, the cells were gently removed and placed into 110 mL of a 25 mM solution of Hepes in Minimum Essential Medium (MEM), supplemented with 10% v/v inactivated calf serum, 1.1 mL of a 200 mM solution of glutamine in 0.85% saline solution, and 11,000 units of penicillin/11,000 mcg streptomycin.

Aliquots (5.0 mL each) of the resuspended cell culture were placed into 50 mL Falcon tissue culture flasks, with or without herbicide, and incubated in the dark at 37° C. for 4 days, the herbicide being added in dilute acetone solution as in Example 1. Acetone was also added to the controls to provide a concentration of acetone of 0.2% v/v therein. The amount of herbicide was such as to provide the concentrations specified in Table 2 below.

The treating agents were:
B As in Example 1
C. As in Example 1
F. A herbicide of the formula:

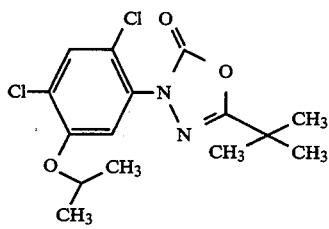

Extraction: The media from each of the flasks were placed in glass round bottom tubes, while the cells adhering to the bottom of the flasks were loosened by the addition of 0.5 mL of a 0.25% solution of trypsin in PBS, and after several minutes at 37° C., then washed from the flasks and recombined with their media. Aliquots of 100 μL were then removed from each cell suspension to determine cell density. The remaining 5.4 mL of cell suspension was then sonified for 30 minutes to disrupt the cells.

Ten mL of basic acetone (90% acetone: 10% 0.1N NH4OH) was then added to each tube, and the tubes were centrifuged to remove protein and cell debris. Five mL of water was added to the supernatant, followed by 0.5 mL of a saturated aqueous solution of NaCl. The pH was then adjusted to 6.8 by the dropwise addition of 2M KH2PO4. The aqueous acetone extract was then loaded onto a C8 Baker Prep column. The columns were dried and then washed with 2 mL of water. The tetrapyrroles were eluted with 3 mL of 90/10 CH3OH/H2O. As in Example 1, all these extraction procedures were carried out substantially entirely under non-protoporphrin IX- exciting light (e.g. green light) or in the dark (e.g. in opaque covered containers). The fluorescence of the extracts was then determined on a SPEX spectrofluorometer. Protoporphyrin IX ("Proto IX") accumulation was quantified utilizing predetermined extinction coefficients. Results are given in Table 2 below.

TABLE 2

Mean Growth Inhibition and Proto IX Accumulation

| Agent | Concentration of Agent (μM) | % Growth Inhibition | Amount of Proto IX (pmoles)** | Relative % Proto IX*** |
| --- | --- | --- | --- | --- |
| B | 100 | 99 | 5.20 | 2364 |
| F | 100 | 106 | 2.71 | 1232 |
| C | 100 | 52 | 4.41 | 2005 |
| C | 10 | −15* | 0.57 | 259 |
| C | 1 | −26* | 0.19 | 86 |

*Negative values for "Growth Inhibition" indicate that growth occurred.
**Average amount per 10^6 cells.
***Percent of control.

Another aspect of this invention relates to the production of protoporphyrin IX ("Proto IX"). In this aspect eukaryotic microalgae are grown heterotrophically in the dark (or under non-Proto IX-exciting light) in a medium containing an agent (described above) which inhibits the enzymatic conversion of protoporphyrinogen to Proto IX. The medium or the algae or both are then treated to extract Proto IX and to separate it from chlorophyll, carotenoids and cell debris, etc. Separation can be in any convenient manner such as by liquid phase chromatography, including reverse phase liquid chromatography, or by solvent extraction, or by precipitating the Proto IX by chelation, as with a metal such as Fe, Zn or Mg, removing the resulting chelate compound and, if desired, regenerating the Proto IX, as by known treatment of the chelate with dilute acid.

The separation steps are carried out under non-Proto IX-exciting light (such as the green light described in Appendix A under the heading "Darkness") or in the dark. The iron chelate is not so light sensitive, so that exposure to light is more permissible when handling that material.

The microalgae are preferably grown as a cell suspension at a temperature in the range of about 15° to 30° C. The concentration of the inhibiting agent may be about $10^{-5}$ to $10^{-7}$M, for instance. Examples of microalgae which may be used are Scenedesmus sp., Chlamydomonas reinhardi, Euglena sp. and Bumilleriopsis filiformis.

EXAMPLE 3

Log phase cultures of Chlamydomonas reinhardi (wild type) are subcultured into a stainless steel vat (e.g. 300 L) using the culture medium described below. An acetone solution of 1-(carbethoxy)ethyl-5-(2-chloro-4-trifluoromethylphenoxy)-2-nitrobenzoate (lactophen, a commercial phenyl ether herbicide) is added to provide a concentration of $10^{-5}$M and a final concentration of acetone of 0.1%. This mixture is allowed to grow in the dark at 25° C. for four to seven days with gentle agitation and/or aeration. While maintaining darkness, the contents of the vat are filtered and the filtrate is treated to recover the protoporphrin IX therein.

One method of treatment to recover the protoporphrin IX is to filter the contents of the reaction vat (while maintaining darkness) and to add acetone to the filtrate. This mixture is extracted with petroleum ether. The aqueous acetone mixture is then extracted with diethyl ether, and the diethyl ether is removed by evaporation to leave a residue. This residue is dissolved in methanol and subjected to reverse phase chromatography to yield protoporphrin IX. Also, the recovery methods described in Examples 1 and 2 may be used.

| Salts | Composition of Medium | | |
|---|---|---|---|
| | Molarity | Stock | mL Stock/L |
| Na Citrate.6H$_2$O | 1.7 × 10$^{-3}$M | 10% | 5 |
| Trace Metals | as below | as below | 10 |
| FeCl$_3$.6H$_2$O | 0.37 × 10$^{-3}$M | 1% | 1 |
| CaCl$_2$.2H$_2$O | 0.36 × 10$^{-3}$M | 5.3% | 1 |
| MgSO$_4$.7H$_2$O | 1.2 × 10$^{-3}$M | 10% | 3 |
| NH$_4$NO$_3$ | 3.7 × 10$^{-3}$M | 10% | 3 |
| KH$_2$PO$_4$ | 2.2 × 10$^{-3}$M | 10% | 3 |
| K$_2$HPO$_4$ | 1.7 × 10$^{-3}$M | 10% | 3 |
| CH$_3$CO$_2$Na | 7.5 × 10$^{-3}$M | 10% | 10 |
| Stock of Trace Metals Mixture | | | |
| H$_3$BO$_3$ | | 100 mg/L | |
| ZnSO$_4$.7H$_2$O | | 100 mg/L | |
| MnSO$_4$.4H$_2$O | | 40 mg/L | |
| COCl$_2$.6H$_2$O | | 20 mg/L | |
| NaMoO$_4$.2H$_2$O | | 20 mg/L | |
| CuSO$_4$ | | 4 mg/L | |

An alternative to the use of *Chlamydomonas reinhardi* is to use *Scenedesmus, sp.* cultured on the above medium, replacing sodium acetate with glucose.

EXAMPLE 4

This example is the same as Example 3 except that the herbicidal compound 1-(4-chloro-2-fluoro-5-propargyloxyphenyl)-3-methyl-4-difluoromethyl-$\Delta^2$-1,2,4-triazolin-5-one is used in place of lactophen.

EXAMPLE 5

Determination of I$_{50}$ (a) Using enzyme in intact chloroplasts:

Protoporphyrinogen IX ("Protogen IX"). Proto IX was purchased from Porphyrin Products, Logan, Utah and purified as outlined by T. P. Fuesler et al., *Plant Physiol.*, 67, 246–249 (1981). Protogen IX was freshly prepared by reduction of Proto IX with a Na/Hg amalgam as outlined by N. J. Jacobs and J. M. Jacobs, *Enzyme*, 28, 206–219 (1982), utilizing the purified Proto IX at a concentration of 300 μM.

Plant Material. Cucumber (*Cucumis sativus* L. cultivar 'Wisconsin SMR18') was raised in a dark growth chamber on vermiculite irrigated with a commercial (9-45-15) fertilizer. The seedlings were grown at 25° C. and a relative humidity of 80 to 90%. Intermittent illumination, one minute of light per 60 minute cycle with a measured intensity of 25 μE/m$^{-2}$ sec$^{-1}$ (PAR), was supplied by a General Electric 'Bright Stick' controlled by an electronic timer. This provided tissue capable of rapid chlorophyll synthesis while minimizing starch reserves and initial chlorophyll levels.

Chloroplast Isolation. Developing chloroplasts were isolated as described by T. P. Fuesler et al., *Plant Physiol.*, 75, 662–664 (1984), except that in the final purification step, plastids were centrifuged through a 40% rather than 45% (v/v) Percoll cushion. The chloroplasts were resuspended in an assay buffer containing 0.5M mannitol, 20 mM TES, 10 mM HEPES, pH 7.7, 1 mM EDTA, 1 mM MgCl$_2$, 1% (w/v) bovine serum albumin and 1 mM dithioerythritol to a final concentration of 2 mg protein/mL.

Assays of Protoporphyrinogen Oxidase. Assays were conducted as outlined by J. M. Jacobs and N. J. Jacobs, *Arch. Biochem. Biophys.*, 229, 312–319 (1984). Samples (0.2 mL) of the chloroplasts suspension were preincubated in the dark for 15 minutes with various concentrations of acifluorfen-methyl ("AFM") or with 0.2% (v/v) acetone (as a "control"). Then fifty ML of freshly prepared Protogen IX (about 15 nM), was added to the suspension to initiate the reaction. Assays were terminated by the addition of 2.75 mL of the fluorometric media of N. J. Jacobs and J. M. Jacobs, *Enzyme*, 28, 206–219 (1982) consisting of 1% (v/v) Tween-20 (polyoxyethylene sorbitan monolaurate), 50 mM Tris-HCl, pH 8.5, 1 mM EDTA; 1 mM dithioerythritol ("DTE") was substituted for 5 mM gluthathione. The suspensions were then read directly on a SPEX Fluorolog-2 spectroflourometer equipped with a frontface fluorescence option for turbid biological samples. The amount of Proto IX produced was quantified from a standard curve (of quantity of Proto IX versus emission at 630 nm, on excitation at 400 nm) generated from purified Proto IX in fluorometric media.

To determine the amount of nonenzymatic oxidation to Proto IX in the above assay, the same assay was carried out except that in place of the suspension of active chloroplasts, there was used a suspension in which the chloroplasts had been inactivated by heating for 15 minutes at 85° C. Substracting the quantity of Proto IX thus produced from the quantity produced in the presence of the active chloroplasts gave the amount of Proto IX formed enzymatically. The results are shown graphically in FIG. 1 (in which LSD indicates least significant difference, as is conventional). FIG. 1 shows that the I$_{50}$ value (the concentration which provides 50% inhibition) is less than 0.1 μM, i.e., about 0.03 μM.

Assays of the effect of 10 μm AFM on the enzymatic conversion of Proto IX to magnesium Proto IX in the chloroplast suspension (in the presence of ATP) showed that AFM had no inhibiting effect on that conversion.

(b) Using isolated enzyme:

Plant Material and Homogenization: Peas (*Pisum sativum* var. Little Marvel) germinated at 20° C. in a dark growth chamber ten days. Plants were illuminated for one hour per day, which allowed for significant leaf expansion while minimizing chlorophyll synthesis. Leaves were pale yellow-green in color.

The leaves were then homogenized in 500 mL of grinding media consisting of 0.5M mannitol, 10 mM HEPES, 20 mM TES, 1 mM EDTA, 1 mM MgCl$_2$, 5mM cysteine, and 0.2 BSA, pH 7.7. The brei was then passed through four layers of cheesecloth, then through a 43-micron nylon mesh. The hemogenate was then centrifuged at 4000 g for 3 minutes. The resultant pellet was utilized for plastid isolation.

Etioplast Isolation and Purification: The pellet (plastid fraction) was resuspended in 40 mL of assay media (grinding media minus cysteine and containing 1 mM DTE and 1% ESA) and centrifuged at 150 g to remove cellular debris. The resultant supernatant was centrifuged at 4000 g, and the resuspended pellets were overlaid on 40% Percoll. After centrifugation for 3 minutes at 6500 g, intact etioplasts pelleted at the bottom of the tube.

Protein content was determined utilizing the BioRad method.

Enzyme Solubilization: The enzyme was solubilized following the procedure of Jacobs and Jacobs. The plastids were pelleted and resuspended in 2.5 mL of buffer consisting of 20 mM Tris-MCl, 30% glycerol, and 1 mM DTE, pH 7.6. After sonification at 60 mHz, a volume of detergent extraction media, 10% Triton 100X, 8% KCl, and 10 mM PMSF, was added to give a final detergent:protein ratio of 0.7 (W/W). After three hours at 48° C., the membrane preparation were ultra-centrifuged at 100,000 g for 1 hr. on a Beckman L2-65B.

Gel Filtration: The supernatants containing the solubilized enzyme were then desalted on a Pharmacia PD-10 G-25M Sephadex column. Columns were washed with 25 mL of Elution Buffer (20 mM Bistris-HCl, 20% glycerol, 0.1% Triton X, pH 6.8). Samples were loaded onto the column and eluted with 3.5 mL of buffer. The first mL fraction was discarded while the remaining 2.5 mL was collected. These fractions were then frozen under $N_2$ at $-77°$ C.

Purification Utilizing DEAE Chromatography: A 0.75 mL volume of plastid-solubilized-enzyme preparation was loaded onto a Waters Protein-Pak DEAE-5PW column (8 mm×7.5 cm) equilibrated with Elution Buffer. After 60 minutes of washing with Elution Buffer (1 mL/minute), the enzyme was eluted with a linear 0.1M NaCl gradient over 100 minutes. The gradient was then changed from 0.1M NaCl to 0.8 M NaCl in 30 minutes. Four-mL fractions were collected and assayed for activity. Peaks were detected using a Waters 494 UV detector at 260 nm, sensitivity:1 AU.

Protoporphyrinogen Oxidase Activity: Enzymatic conversion of protoporphyrinogen IX to protoporphyrin IX was assayed as described in section (a) of this Example 5.

In this test, compound 6c (of Example 6 below) showed $I_{50}$ values of 0.8 to 0.3 μM (corresponding to a $pI_{50}$ of 6.1 to 6.5, where $pI_{50}$ is negative log of the $I_{50}$ Molarity); for AFM the value was 0.08 μM ($pI_{50}$ of 7.1) and for compound 8v (of Example 8 below) the value was 0.08 to 0.03 μM ($pI_{50}$ of 7.1 to 7.5).

EXAMPLE 6

In this Example the enzyme-inhibiting agents were added to the feed of tumor-bearing mice; for some of the mice, used as a control, no agent was added to the feed. The mice were then sacrificed and their kidneys, intestines, adrenal glands, liver and tumor were removed and analyzed for their content of Proto IX. The following enzyme-inhibiting agents were employed:

6a.

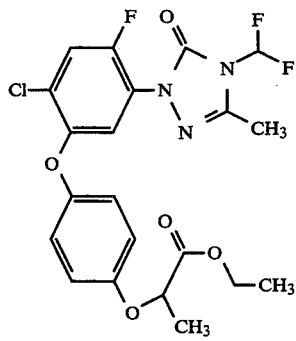

6b.

-continued

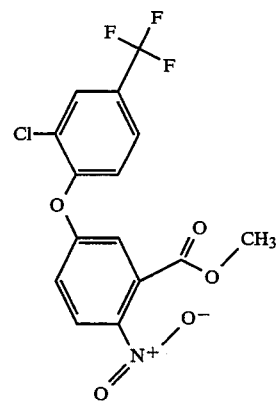

6c.

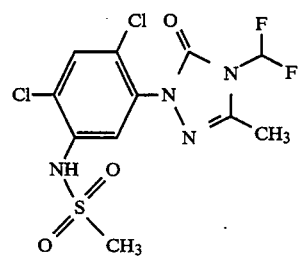

6d.

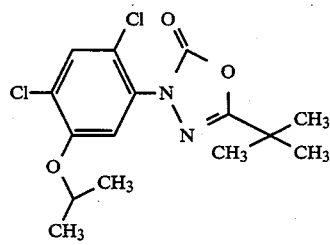

6e.

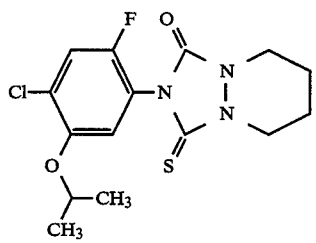

6f.

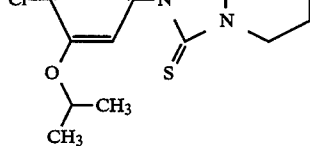

6g.

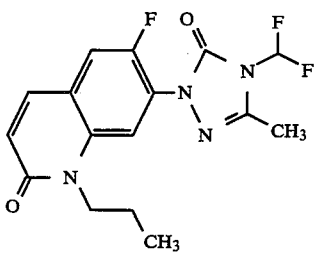

6h.
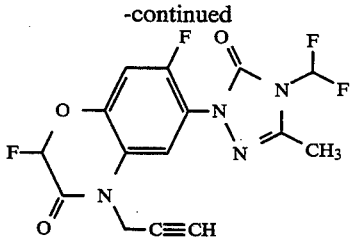

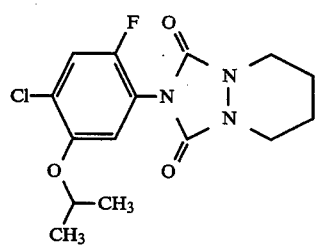

6i.
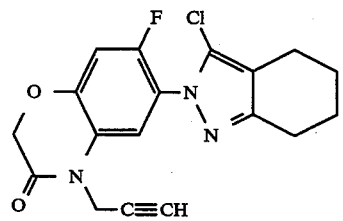

6j.
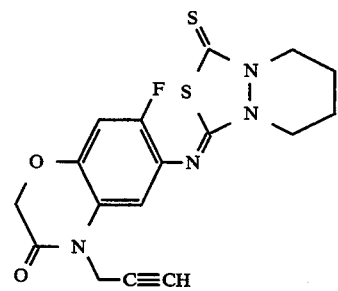

More particularly, the mice were DBA/2 Ha mice which had been injected with SMT-F subcutaneous tumors on Day 0 in the right shoulder. The mice, individually housed, received untreated Purina Rodent Chow 5001 Mash on Day 1; thereafter on Days 2 through 10 the mice received the same Mash treated with 2000 ppm of the inhibiting agent being tested (or, for the controls, the same untreated Mash). The treatment of the Mash was effected by blending it with a small amount of an acetone solution of the agent to be tested. The mice were then sacrificed on Day 10, except for the mouse treated with the agent designated as 6j; the latter was sacrificed on Day 7. The tissues were refrigerated at 4° C. overnight, then blotted dry, and the fresh weight of each tissue sample was recorded. The tissues were then homogenized in 5 mL, or 10 mL in the cases of intestines and liver, of acetone-0.1N NH4OH (9:1, v/v). The homogenates were then centrifuged at 1500 g and the supernatants were analyzed on a SPEX FA112 spectrofluorometer; excitation 400 nm, emission 630 nm wavelengths, the optima for Proto IX. Proto IX accumulation was determined as CPS (fluorescent counts per second emitted) per gram of tissue. The results are tabulated below (results are averages for two mice for each treatment, except for treatments with agents 6f, 6h, 6i and 6j in each of which only one mouse was treated):

| Agent | Proto IX Mean Cps per gram × $10^3$* | | | | | Weight of Tumor as excised (mg) |
| --- | --- | --- | --- | --- | --- | --- |
| | Tumor | Liver | Kidneys | Adrenal | Intestine | |
| 6a | 1203 | 4291 | 10817 | 6572 | 5870** | 143 |
| 6b | 1520 | 1261 | 2441 | 2529 | 5577** | 90 |
| 6c | 14336 | 2739 | 16186 | 13790 | 9937** | 157 |
| 6d | 2006 | 1581 | 12865 | 443 | 5565** | 294 |
| 6e | 837 | 876 | 915 | 1331 | 2069** | 165 |
| 6f | 449 | 1170 | 661 | 5611 | 1157 | 69 |
| 6g | 166 | 803 | 606 | 1984 | 466 | 250 |
| 6h | 298 | 914 | 585 | 2259 | 584 | 192 |
| 6i | 932 | 1510 | 4014 | 36940 | 3454 | 20 |
| 6j | 1251 | 538 | 315 | 491 | 572 | 11 |
| Control | 239 | 536 | 494 | 1504. | 233 424** | 200 |

*Numbers in the table equal raw data × $10^{-3}$.
**Measurements were made on samples diluted with 3 parts basic acetone to one part sample.

These figures correspond to the following concentrations of Proto IX in the respective tissues, expressed as ug of Proto IX per gram of tissue:

| Agent | Tumor | Liver | Kidneys | Adrenal | Intestine |
| --- | --- | --- | --- | --- | --- |
| 6a | 11 | 39 | 99 | 60 | 54 |
| 6b | 14 | 12 | 22 | 23 | 51 |
| 6c | 131 | 25 | 148 | 126 | 91 |
| 6d | 18 | 14 | 117 | 4 | 51 |
| 6e | 8 | 8 | 8 | 12 | 19 |
| 6f | 4 | 11 | 6 | 51 | 11 |
| 6g | 2 | 7 | 6 | 18 | 4 |
| 6h | 3 | 8 | 5 | 21 | 5 |
| 6i | 9 | 14 | 37 | 337 | 32 |
| 6j | 11 | 5 | 3 | 4 | 5 |
| Control | 2 | 5 | 5 | 14 | 2 4 |

The article by Dougherty cited above gives a figure of 3.6 ug/g for the concentration of the porphyrin in the same type (SMT-F) of tumor after injection of 10 mg/kg of hematoporphyrin derivative into the same type (DBA/2 Ha) of mice. Other technical literature (Moan et al P&P 46-5, pages 713–721; note FIG. 2 on page 716) indicates that a concentration of about 12 ug/g of the porphyrin is attained in tumors (C3H/Tif mammary carcinoma) in DBA/H2 mice after intraperitoneal injection of 25 mg/kg of Photofrin II, the widely used sensitizer for photodynamic treatment and detection of cancer.

The total amounts of agent-containing feed consumed by the mice were as follows: 6a, 22 and 35g; 6b, 37 and 35g; 6c, 25 and 22g; 6d, 41 and 32g; 6e, 40 and 44g; 6f, 27g; 6g, 33 and 40g; 6h, 36g; 6i, 10g; 6j, 20g.

In preparation for the experiments described in this Example 6, the following routine steps were carried out, using (unless otherwise noted) the agent which is designated 6c in that Example, with non-tumor-bearing animals:

a. The $LD_{50}$ of the agent was determined to be over 2600 mg/kg (i.e. mg of the agent per kg of body weight) for rats (determined during a 14-day period following a single oral dose comprising corn oil containing 15% of the agent) and over 700 mg/kg for mice (determined during a 14-day period following a single oral dose comprising corn oil and 5% of the agent).

b. In tests of vehicles for injection intraperitoneally, without the agent, it was determined that the mice could tolerate injection of a 0.5 mL dose of a mixture of equal parts of DMSO (dimethylsulfoxide) and water.

c. In tests of the agent injected intraperitoneally in a mixture of 60% corn oil and 40% DMSO it was determined that the mice could tolerate a dose of 100 mg/kg.

d. The following trials were carried out with mice:
   i. daily oral gavage of 50 mg/kg (using a 1% solution of the agent in acetone) for eight days;
   ii. daily I.P. injection of 50 mg/kg (using a 1% dispersion of the agent in mineral oil, made by dissolving the agent in a drop of DMSO and mixing the resulting solution with the mineral oil) for eight days;
   iii. daily topical application to the skin of 50 mg/kg (using a 1% solution in DMSO) for eight days;
   iv. feeding for eight days of a standard feed into which there had been incorporated 2000 ppm of the agent, based on the weight of the feed;
   v. daily I.V. injection of 50 mg/kg (using a 2% solution in DMSO) for four days.

The mice used in these trials were then sacrificed and their tissues examined for Proto IX accumulation.

In another test, a male Fisher 344 rat was fed for 27 days with feed containing 5000 ppm of agent 6c and then sacrificed. The tissues of this rat showed increased levels of Proto IX as compared to a control, with marked increases in the levels in the kidney, intestine, stomach and brain and only a small increase in the level in muscle tissue.

In the foregoing tests of rats and mice the animals were kept on a standard 12 hr. dark-12hr. light cycle.

EXAMPLE 7

In a series of experiments along the lines of Examples 1 and 2, cultures of HeLa cells were incubated in the presence of 100 μM of various treating agents, listed below. The percentage given, next to each treating agent, indicates the increase in the amount of Proto IX produced in the presence of that treating agent relative to the amount produced by the control in the same experiment.

Agents used in Examples 6: 6a, 337%; 6b, 366%; 6c, 297%; 6d, 1200%; 6e, 1210%; 6f, 280%; 6g, 326%; 6h, 431%; 6i, 544%; 6j, 469%. Other agents:

7a. 136%

7b. 229%

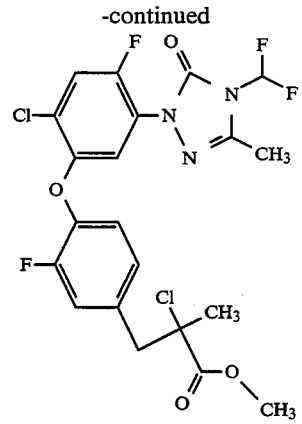

7c. 20%

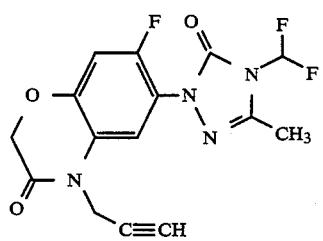

7d. 115%

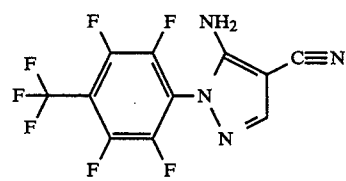

7e. 400%

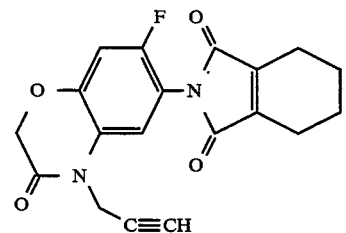

7f. 122%

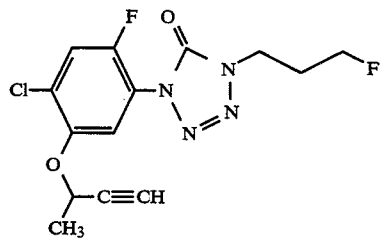

7g. 303%

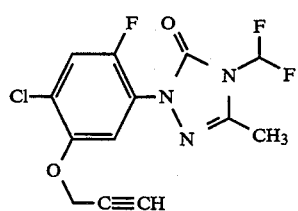

-continued

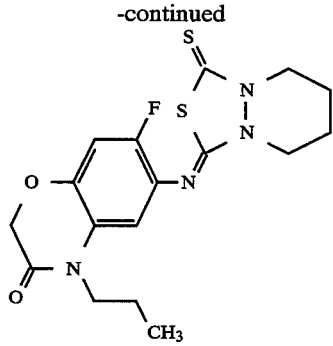

7h. 97%

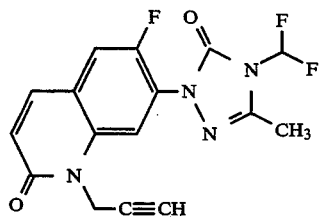

As in Examples 1 and 2, the data for this Example 7 were based on measurements of fluorescence (e.g. in counts per second, "cps"). In this Example, however, the measurements were made on an extract of the cells alone (in contrast to Examples 1 and 2 in which the disrupted cells and culture medium together were extracted), the fluorometric medium was the one described in Example 5 (containing 1% Tween-20, 50 mM Tris-HCl, 1 mM EDTA and 1 mM dithioerythritol, pH 8.5), and a cps measurement of the fluorometric medium per se was also made. In calculating the foregoing data for this Example, the following formula was used to calculate the percentage increases:

$$\left[\frac{C_a - C_m}{C_c - C_m} \times 100\right] - 100$$

where $C_a$ is the counts per second for the sample resulting from treatment with the agent, $C_c$ is the counts per second for the control sample, and $C_m$ is the counts per second for the fluorometric medium per se (i.e. the background fluorescence). On reviewing the data it was observed that $C_c$-$C_m$ for this set of experiments was relatively small compared to $C_m$; for instance, individual measured values were 49025 and 52069 for $C_c$ and 4295 for $C_m$. Consequently, the use of the foregoing formula did not give a good indication of the effectiveness of the compound. Accordingly, the data were recalculated using the formula:

$$\frac{C_a}{C_c} \times 100$$

with the following results: 6a 336%; 5b 148%; 6c 154%; 6d 510%; 6e 320%; 6f 280%; 6g 329%; 6h 178%; 6i 171%; 6j 185%; 7a 118%; 7b 142%; 7c 103%; 7d 128%; 7e 173%; 7f 118%; 7g 155%; 7h 118%.

EXAMPLE 8

In this Example the Proto IX contents of treated HeLa cells and their culture media were separately analyzed, demonstrating that a large part of the Proto IX formed in the cells during the treatment is secreted into the culture medium.

In a manner similar to Examples 1 and 2, cultures of HeLa cells were incubated in the presence of 100 µM of various treating agents, listed below. The agent was added in dilute solution in dimethylsulfoxide (DMSO),and the controls contained 0.2% DMSO v/v. After such incubation the culture medium was poured off, removing it from the cells, the cells were loosened from the culture flasks by addition of 0.25% w/v trypsin which remained in contact with the cells for 20 minutes at 37° C., after which a fluorometric medium was added to the flask. The fluorometric medium was the same as that described in Example 7 except that its pH was 6.5; this medium also acted as an extractant. The resulting extract was analyzed for Proto IX content. The separated culture medium was also analyzed fluorometrically for Proto IX content. The pairs of percentages given, next to each treating agent, indicate the amount of Proto IX produced in the presence of that treating agent relative to the amount produced by the control in the same experiment; the first number of each pair relates to the concentration of Proto IX in the culture medium and the second number relates to the concentration in the cells.

8a. 218%, 127%

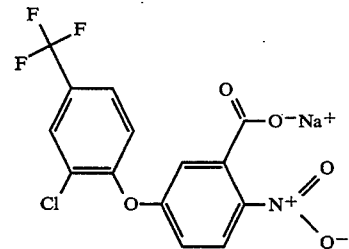

8b. 722%, 193%

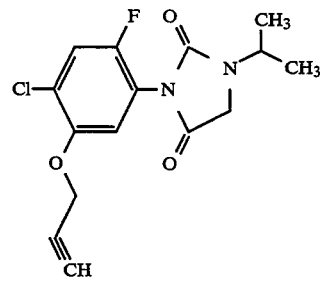

8c. 134%, 106%

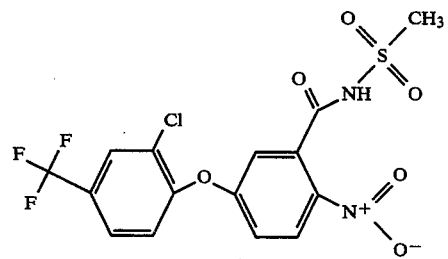

8d. 105%, 101%

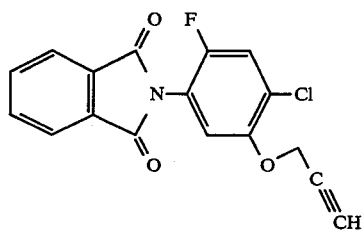
8e. 107%, 98%
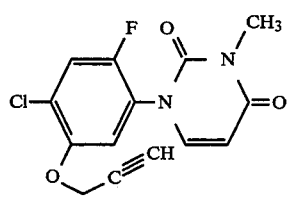
8f. 207%, 108%
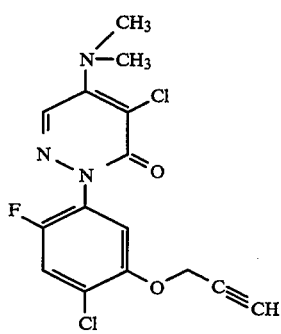
8g. 149%, 105%
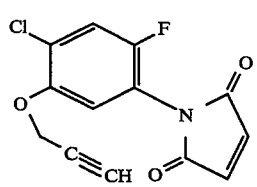
8h. 776%, 252%
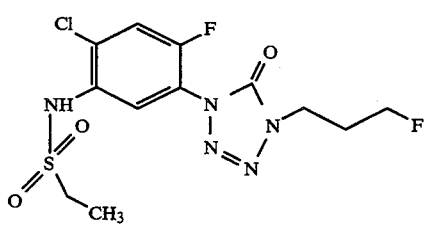
8i. 101%, 99%
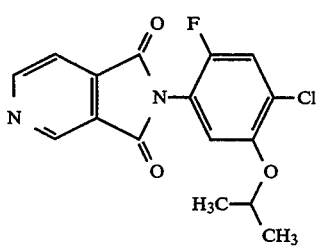
8j. 153%, 105%
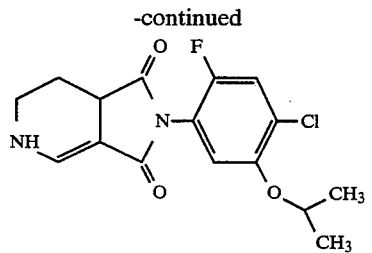
8k. 124%, 102%
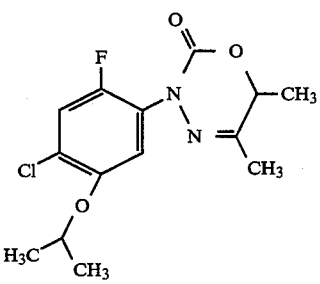
8l. 129%, 100%
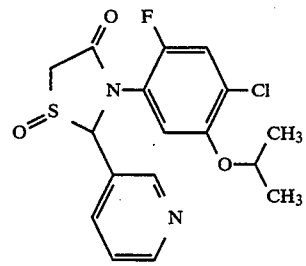
8m. 289%, 134%
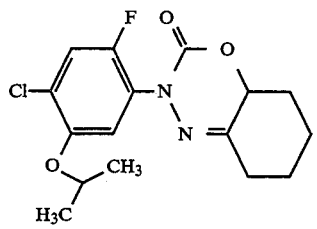
8n. 297%, 135%
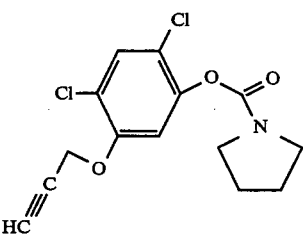
8o. 112%, 103%
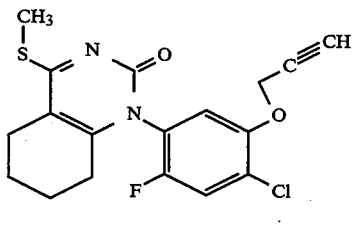
8p. 110%, 96%

-continued
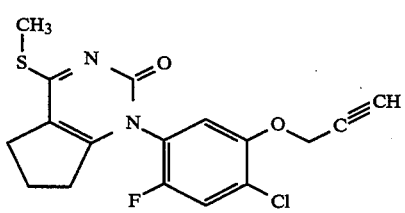
8q. 120%, 101%
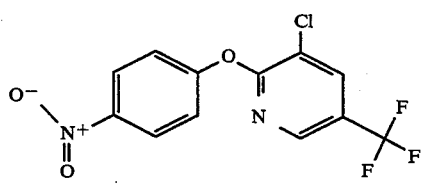
8r. 140%, 102%
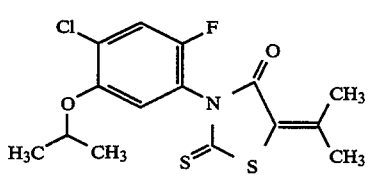
8s. 115%, 106%
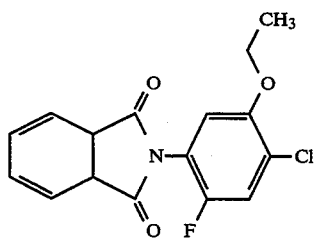
8t. 150%, 105%
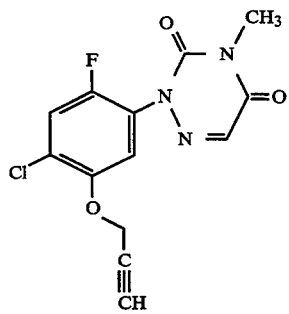
8u. 122%, 100%
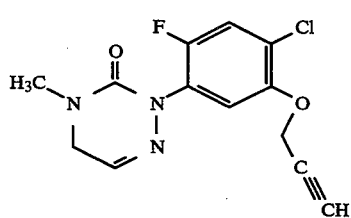
8v. 172%, 111%
-continued
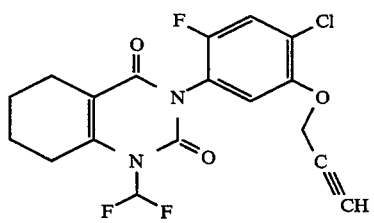
8w. 121%, 102
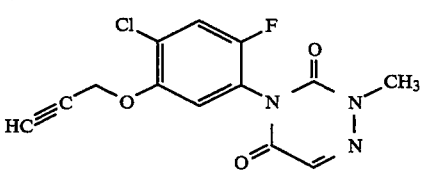
8x. 192%, 118%
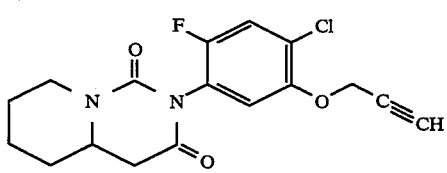
8y. 126%, 101%
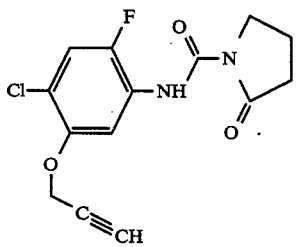
8z. 183%, 112%
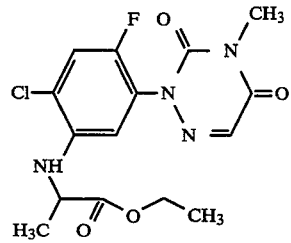
8aa. 101%, 100%
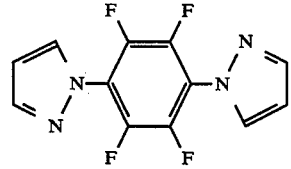
8ab. 122%, 101%
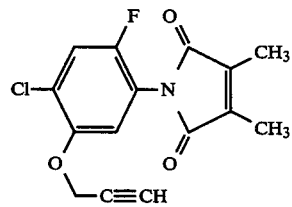
8ac. 123%, 101%

-continued
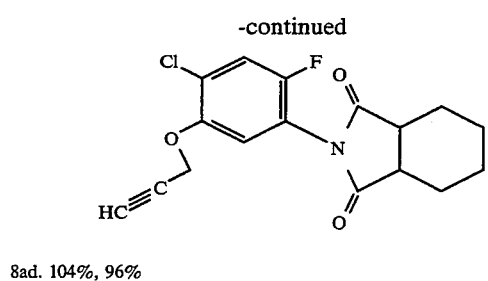
8ad. 104%, 96%
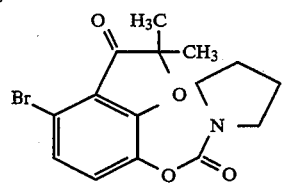
8ae. 126%, 101%
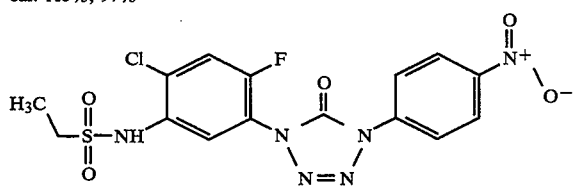
8af. 115%, 97%
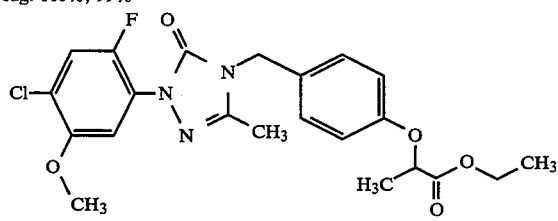
8ag. 110%, 99%
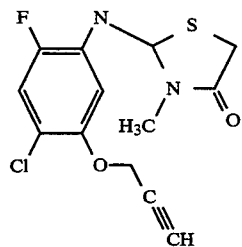
8ah. 109%, 97%
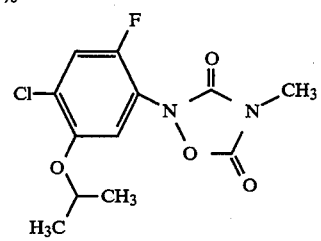
8ai. 200%, 118%
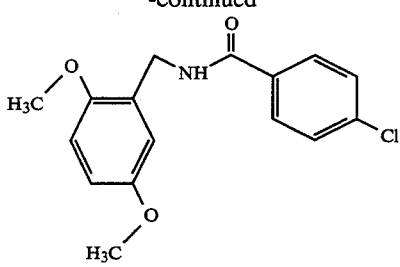
8aj. 104%, 100%
-continued
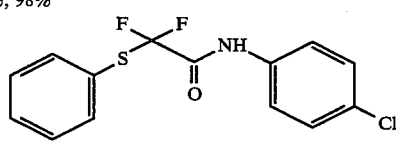
8ak. 110%, 98%
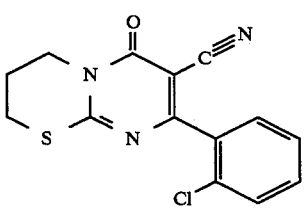
8al. 102%, 98%
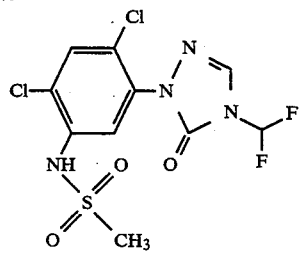
8am. 434%, 191%
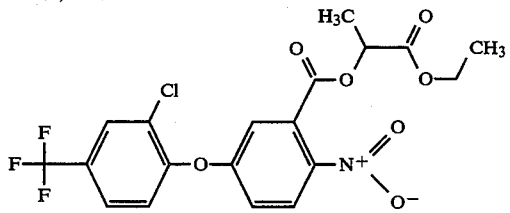
8an. 712%, 291%
8ao. 587%, 214%
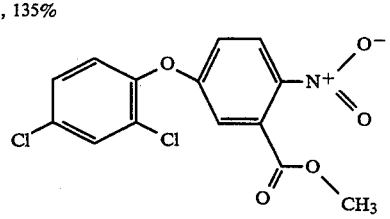
8ap. 304%, 135%
8aq. 210%, 126%

-continued

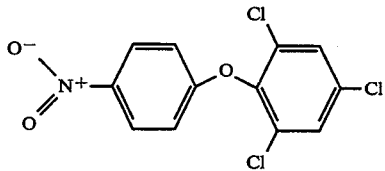

8ar. 122%, 106%

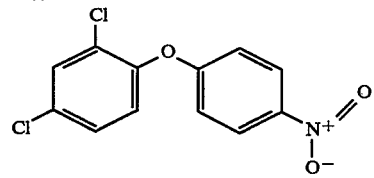

6b. 271%, 142%

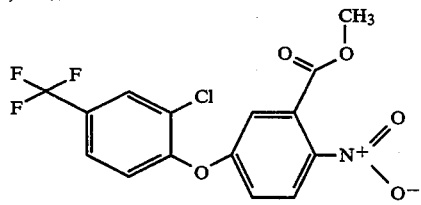

6c. 772%, 280%

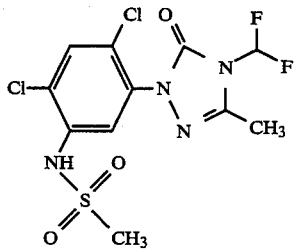

6e. 690%, 256%

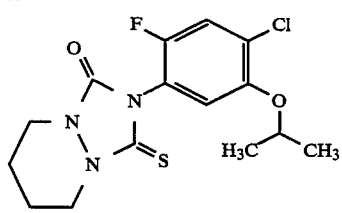

For compounds 8t-8ar, rough observations of cell growth as compared to the control indicated that certain of the agents had an inhibiting effect on cell growth as follows:

8aj, ag, ar: 25% inhibition
t, ac, ai, ak, an, ap: 50% inhibition
u: 60% inhibition
v: 90% inhibition
ab, ad, ae, af, ah: lethal

EXAMPLE 9

In this Example the enzyme-inhibiting agent 6c of Example 6 was fed to rats, tumors were implanted in the rats and the tumor-bearing zone was exposed to light, causing regression of the tumors.

Specifically, three Sprague-Dawley rats of average weight 120 g were placed on a diet of feed containing 2000 ppm of the agent for a period of 6 days. On day 3, chondrosarcoma was implanted into the right hind limb of each rat by injecting 0.3 mL of a suspension of the tumor cells (about one million tumor cells). On day 6 the right hind limb of each rat was shaven and depilated, the size of each tumor was measured, and the tumor area and surrounding skin were then exposed to non-thermal doses of 630 nm light for a total of 270 J/cm². On the next day, two of the rats were found to be apparently free of their tumors (that is, no palpable tumor mass), and the third rat showed almost complete regression of its tumor. The surrounding skin and muscle tissue of the rats were slightly blanched and showed some swelling, significantly less than is encountered with Photofrin II-mediated photodynamic therapy.

In another set of experiments, 20 of the rats were placed on the same diet as above (i.e. feed containing 2000 ppm of agent), provided ad libitum, for 10 days before the treatment with the light, and the injection of the tumor cell suspension was made after the animals had been on the diet for 7 days. Such an injection causes the formation of a tumor having a well defined vascular network within 1 to 2 days. At the time of the treatment with light the tumors had diameters of 5-8 mm and were free of evident necrosis. On the day following the light treatment visible regression was observed in 75% of the tumors treated; this regression was marked by a lack of palpable tumor mass, with some darkening over where the tumor had been. However, over time some 95% of the tumors regrew, indicating that this particular light treatment had left some viable tumor cells and that modification of the treatment, in one or more of the following ways, would be desirable: longer light treatment; one or more additional light treatments; higher dose of agent; exposure of the tumor cells to the enzyme-inhibiting agent for a longer period than 3 days; change in the mode of administration, e.g. injecting.

The light treatment used did not cause apparent occlusion of blood flow to the treatment area, as demonstrated on injection with sodium fluoroscin immediately after the exposure to light.

In a duplication of the preliminary test on rats, using oral administration, treatment with compound 8c (an agent much less active than compound 6c in the test in Example 8) at the same dosage did not produce any regression of the tumors.

EXAMPLE 10

In this Example preliminary routine dosage experiments, using agent 6c of Example 6, were made, using female DBA/2 mice, four to six weeks old (14-18 grams). For tumor implantation into these animals, SMT-F tumor was aseptically removed from donor animals and cut into 1 mm³ fragments. These tumor pieces were placed in Hank's Balanced Salt Solution containing penicillin and streptomycin. Tumor pieces were implanted via a trochar into the center of the right flank of shaved mice. Tumors were found to reach a diameter of 5-7 mm. in eight days. The skin covering and surrounding the tumor was shaved and depilated two to three hours prior to light treatment.

The light treatment employed red light centered on 630 nm obtained from 1000 watt Xenon arc lamp system (Oriel Corporation) using a condenser which focused the light into a trifurcated fiberoptic bundle. A collimating lens was placed at the end of each fiberoptic in order to focus the image of the fiberoptic bundle on the treatment area; a spot of 1.3 mm in diameter (1.33 cm²). The design of the fiberoptic bundle ensured uniform distribution of light over this area. The output spectrum of the arc lamp was tuned to a peak intensity of 630 nm (602-670 nm range) using a water filter, a heat reflecting filter, and a 610 nm long pass filter. Light was delivered at a power density of 135 mW/cm$^2$. The possibility of tissue hyperthermia induced by this power density was evaluated by placing thermocouples at selected depths into the tumor during treatment, and measuring any temperature rise. No increase in tumor temperature greater than 2.4° C. (final temperature of 37.5° C.) was observed. During the light treatment the mice were restrained without anesthesia in specially designed holders and the tumors and surrounding skin were exposed to light to different degrees, fro 0 to 600 J/cm$^2$.

Animals were examined daily for tumor regression or regrowth for 14 days post-treatment, and weekly for up to a total of 91 days post-treatment. Mice which remained tumor free at 35 days post-treatment were considered cured. No tumor regrowth was noted in any mice between 35 and 91 days post-treatment.

When the mice were given 4000 ppm of the inhibiting agent in their feed (rodent chow, ad libitum) for a total of three days and then treated with 450 J/cm$^2$ of light, the tumors were cured in about 33% of the mice.

In the course of the experiment the porphyrin fluorescence at 650 nm of the tumors (on exposure to fluorescing-inducing light at 630 nm) was measured with a fluorescence photometer. All animals showed an increase in tumor fluorescence, but some animals showed slightly higher fluorescence levels than others on the same diet and those (higher fluorescing) animals had higher cure rates.

It may be convenient to screen the enzyme inhibitors (such as known "peroxidizing herbicides") by testing the effect of the compound on the production of protoporphyrin IX in cultures of HeLa cells (as in Examples 1, 2, 7 and 8 above). Instead of HeLa cells one may employ other cell lines such as undifferentiated mammalian cells, e.g. lymphoma cells, mouse leukemia cells, human fetal lung fibroblasts, Chinese hamster ovary cells, or any other mammalian cell line that reproduces or makes heme.

Still another aspect of this invention relates to insecticides. Rebeiz et al, in Pesticide Biochemistry and Physiology 30, pages 11–27 (1988), describe porphyric insecticides comprising 2,2' dipyridyl ("DPY", which is described as a "modulator" of the porphyrin-heme biosynthetic pathway) with or without ALA. The enzyme-inhibiting agents of this invention may be used in place of the DPY (and in much smaller amounts, if desired) for the same insecticidal purpose, with or without ALA. For instance the following compounds were tested and found to be active against mosquito larvae: 8h, 1B (compound B, of Example 1), 7f, 6a and a compound of the formula:

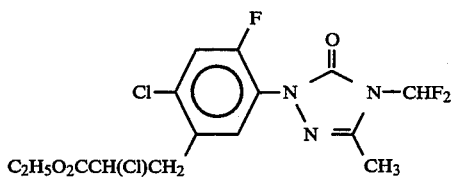

Compounds 1B and 7f were found to be active against cabbage loopers.

APPENDIX A

Percent Efflux Test

The Percent Efflux test employs cotyledons harvested from etiolated cucumber seedlings. In an initial step a mass of cotyledons is treated in the dark with an aqueous buffered solution containing a radiolabelled sugar. The amount of the sugar taken up by the cotyledons is then measured (by counting, as described below). The mass of cotyledons is then divided into two portions; one portion of the cotyledons is treated in the dark with an aqueous buffered solution containing the compound to be tested, while the other portion is treated in the same way, in the dark, with an otherwise identical solution without the test compound, as a control. The cotyledons, in contact with the aqueous solutions, are then exposed to light for 16 hours, and then separated from the aqueous solutions; the latter are then measured (by counting) to determine their contents of radiolabelled material. The results are expressed as Percent Efflux which is calculated as follows, where S is the count of radiolabelled material (per cotyledon) taken up by the cotyledons in their initial treatment, $S_T$ is the count of radiolabelled material (per cotyledon) in the aqueous solution containing the compound to be tested, after the exposure to light and $S_c$ is the count of radiolabelled material (per cotyledon) in the aqueous solution of the control, after exposure to light:

$$\text{Percent Efflux} = \frac{S_T \text{ minus } S_c}{S}$$

More specifically, the following materials and conditions are employed in the Percent Efflux test.

Plant material: Cucumber seed (Cucumis sativus L. cultivar 'Wisconsin SMR 18') was germinated and grown in vermiculite irrigated with a commercial (9-45-15) fertilizer. Seedlings were grown at 25° C. and 80–90% RH in a dark incubation chamber. Cotyledons were harvested from the etiolated seedlings five days after planting and were rinsed in 1.0 mM CaCl$_2$, all under green light.

Buffered solution: 1 mM KCl, 1 mM CaCl$_2$ and 2.0 mM potassium phosphate, adjusted to pH 6.5 (as with NaOH).

Radiolabelled sugar: 3-0-methyl-3-[U-14C]glucose of specific activity 10.9 GBq/mmol (Amersham Corp., Arlington Heights Ill.).

Initial treatment: Washed cotyledons (180 to 230) are added to a 250 mL widemouth foam-stoppered Erlenmeyer flask containing 50 mL of the buffered solution, and the radiolabelled sugar is added in an amount to give a concentration of 600 nM thereof in the solution. The flask is shaken for 24 hours at 125 rpm on a gyratory shaker in the dark. The cotyledons are then recovered on a nylon mesh and rinsed three times in 20 mL volumes of 1 mM CaCl$_2$. The uptake of the radiolabelled sugar is measured by digesting three samples of five cotyledons each in NCS tissue solubilizer (Amersham Corp.) and counting the resulting macerate in a liquid scintillation spectrometer. (Results from these digestions were found to be equivalent to the same determination made by combusting sampled cotyledons in an autooxidizer.)

Treatment with compound to be tested (and control treatment):

Five of the cotyledons are floated, abaxial side up, on 3 mL of the buffered solution in a 35 mm diameter covered plastic petri dish. The test compound is then added (as a solution thereof in acetone) in such amount as to give a predetermined concentration (discussed below) of the test compound in the buffered solution;

the acetone concentration in the buffered solution is then 0.1% (v/v) in the control as well as in the solution containing the test compound. The floating cotyledons are then swirled by shaking the dishes at 90 rpm on the surface of a gyratory shaker for 16 hours.

Exposure to light: The dishes containing the cotyledons floating on the solutions are exposed for 16 hours to illumination provided by four GE F20T12-CW fluorescent lamps at a measured intensity of 150 $\mu E$ m$^{-2}$ sec$^{-1}$ in the photosynthetically active region of the spectrum (PAR) (measured at the surface of the cotyledons) while the dishes are being shaken.

Measurement of amount of radiolabelled material in the liquid: All the liquid is separated from the cotyledons and then counted in a liquid scintillation spectrometer.

Darkness: All treatments prior to the illumination step are carried out in the dark or under green fluorescent light (i.e. light filtered through a green plastic cut-off filter which passes light of 450–600 nm).

Appendix B
Culture Media
Medium M

| Salts | Molarity | Stock | mL Stock/L |
|---|---|---|---|
| Na Citrate.6H$_2$O | $1.7 \times 10^{-3}$M | 10% | 5 |
| Trace Metals | as below | as below | 10 |
| FeCl$_3$.6H$_2$O | $0.37 \times 10^{-3}$M | 1% | 1 |
| CaCl$_2$2H$_2$O | $0.36 \times 10^{-3}$M | 5.3% | 1 |
| MgSO$_4$.7H$_2$O | $1.2 \times 10^{-3}$M | 10% | 3 |
| NH$_4$NO$_3$ | $3.7 \times 10^{-3}$M | 10% | 3 |
| KH$_2$PO$_4$ | $2.2 \times 10^{-3}$M | 10% | 3 |
| K$_2$HPO$_4$ | $1.7 \times 10^{-3}$M | 10% | 3 |

Stock of Trace Metals Mixture

| | |
|---|---|
| H$_3$BO$_3$ | 100 mg/L |
| ZnSO$_4$.7H$_2$O | 100 mg/L |
| MnSO$_4$.4H$_2$O | 40 mg/L |
| COCl$_2$.6H$_2$O | 20 mg/L |
| NaMoO$_4$.2H$_2$O | 20 mg/L |
| CuSO$_4$ | 4 mg/L |

Culture Medium A is prepared by adding 10 mL/L of an aqueous, 10% sodium acetate solution ($7.5 \times 10^{-3}$M) to Medium M.

The components are added to distilled water in the order listed above and are autoclaved at 15 psi for 15 minutes.

Stock Cultures Grown in the Presence of Light

Stock Cultures of y-1 cells are maintained axenically in liquid culture on Medium A or M, preferably on Medium M, in a 14/10 hour light/dark cycle at 25° C. in Erlenmeyer flasks which are stoppered with polyurethane plugs. The stock cultures are incubated without supplemental aeration on rotary shakers at 125 rpm. The light intensity at the culture level is 120 ME m$^{-2}$ sec$^{-1}$ (PAR). Under these conditions the cultures are in a semi-synchronous mode of growth until they reach a stationary phase of $2-4 \times 10^6$ cells/mL.

Cultures Grown Without Light (Dark-Grown Culture)

Cells from the stationary phase of stock cultures grown in the presence of light (7.5 mL) are transferred to 750 mL of Medium A in an Erlenmeyer flask. The cells are incubated in the dark, with aeration through a submersed aeration tube, at 25° C. for three to four days. During this period this culture of y-1 cells will undergo seven to eight cell divisions, losing all visible chlorophyll, and the concentration should be $2-3 \times 10^6$ cells/mL.

Preparation of Cells for Use in Assay

Cells are harvested from a freshly prepared dark-grown culture (750 mL) by low speed centrifugation, i.e., about 2000 rpm, for approximately five minutes at about 20° C. The cells are gently resuspended in 50 mL of Medium A. A sample of this suspension (approximately 0.25 mL) should be examined for motility and, after fixation with an aqueous, 1% gluteraldehyde solution, a cell count should be made to determine the number of cells/mL. A normal cell count is about $5 \times 10^7$ cells/mL. Aliquots of 1 mL ($10^7$ cells/mL) are placed into the testing vessels (e.g., Falcon, 24-well tissue culture plates). At this point the cells are very motile and are yellow in color.

The test compound is dissolved in a solvent (acetone, ethanol, dimethylsulfoxide, or water, preferably acetone) to provide a concentration which is 1000 times the final concentration. One $\mu L$ of this test solution is added to each of two wells with a 5 or 10 $\mu L$ microsyringe.

Four control wells per tissue culture plate are prepared in the manner described above without the test compound present. The tissue culture plates are covered with a transparent plastic cover and are placed in a growth chamber with a light intensity of 70–90 $\mu E$ m$^{-2}$ sec$^{-1}$ for 13–16 hours at 25° C. If the contents of the test wells appear yellow, they are extracted as described in the Evaluation of Results section below. If the contents of the test wells appear transparent or are a pale-green color, they are placed on a rotary shaker at approximately 125 rpm and are irradiated for two hours with a light intensity of about 600 $\mu E$ m$^{-2}$ sec$^{-1}$ before being extracted.

Evaluation of Results

An aqueous, 10% sodium dodecyl sulfate solution (250 ML) and methanol (1 $\mu L$) is added to each test well and is mixed thoroughly. The mixtures are allowed to stand in the dark for three to four hours. The tissue culture plates are centrifuged at room temperature at low speed (ca. 2000 rpm) for five minutes. The supernatants are removed and analyzed in a Beckman Model 35 spectrophotometer between 350 nm and 500 nm for the presence of protophorphrin IX, at 668 nm which is the absorption peak of chlorophyll in this solvent system, and at 720 nm to use as a turbidity background reading.

Analysis of Data

For each well a greenness value is obtained by subtracting the 720 nm reading from the 668 nm reading. These values are averaged for each concentration of the compound to be tested and for the control. The percent inhibition is $$100 \times \left(1 - \frac{\text{Average greenness value for the particular concentration}}{\text{Average greenness value for the control}}\right)$$

We claim:

1. Method for detecting or locating mammalian tumor cells by increasing the porphyrin content of said mammalian tumor cells in mammalian tissue and examining said mammalian tissue under porphyrin-stimulating light and observing the fluorescence from the tumor, which comprises treating an organism comprising said mammalian tumor cells with a compound which is a specific inhibitor of the enzymatic conversion of protoporphyrinogen to heme in mammalian cells and which is not a tetrapyrrole thereby causing a buildup of protoporhyrin IX in said mammalian tumor cells.

2. Method as in claim 1 in which said compound is a specific inhibitor of the enzymatic conversion of protoporphyrinogen to protoporphyrin IX by protoporphyrinogen oxidase.

3. Method as in claim 2 in which said compound has a redox potential more negative than −500 mV.

4. Method as in claim 2 in which said compound has an $I_{50}$ for protoporhyrinogen oxidase of less than about 10 μM.

5. Method as in claim 4 in which said $I_{50}$ is less than about 1 μM.

6. Method as in claim 2 in which said compound is a nitrodiphenyl ether herbicide.

7. Method as in claim 6 in which said nitrodiphenyl ether has a carboxylic acid ester substituent.

8. Method as in claim 7 in which said substituent is a carboethoxyethyl or carboethoxymethyl substituent.

9. Method as in claim 6 in which said nitrodiphenyl ether has an ethoxy or methoxy substituent.

10. Method as in claim 2 in which said compound has the formula Ph—NHet where "Ph" is a substituted phenyl and NHet is a 5- or 6-membered heterocyclic ring having one to four ring-nitrogen atoms and having the formula

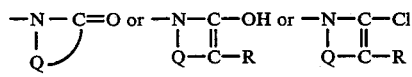

where Q represents the balance of the heterocyclic ring and R represents hydrogen or a substituent group.

11. Method as in claim 2 in which said compound has the formula

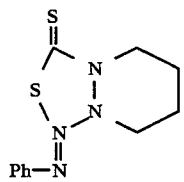

where Ph is substituted phenyl.

12. Method as in claim 2 in which said compound has the formula

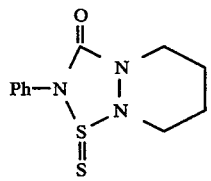

where Ph is substituted phenyl.

13. Method as in claim 10 in which Ph is phenyl having a substituent of the formula

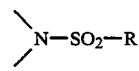

where R is lower alkyl.

14. Method as in claim 10 in which Ph is phenyl having a substituent which includes a terminal 1-(lower alkoxycarbonyl)ethoxy group.

15. Method as in claim 10 in which said substituent is a phenoxy substituent.

16. Method as in claim 2 in which a mammal having a solid tumor is treated with said compound, after which the tumor is subjected to the porphyrin-stimulating light.

17. Method as in claim 16 in which said treatment with said compound comprises oral administration of said compound to said mammal.

18. Method as in claim 17 in which said compound is a water-soluble salt or an acidic compound whose sodium salt is water soluble.

19. Method as in claim 10 in which said compound is an aryl triazolinone, an aryl tetrazolinone, an aryl triazinedione, an aryl oxadiazole, an aryl tetrahydroindazole, an aryl tetrahydrophthalimide, an aryl hydantoin, an aryl urazole, an aryl hexahydropyridazine, an aryl pyrazole, an aryl imidazolopyrimidine, an aryl pyridyldiazine, an aryl diazinedione, an aryl pyradiazinone, an aryl oxadiazolinone, an aryl oxadiazinone, an aryl benzamidazole, an aryl iminotriazolopyridazine, an aryl thiazole, or an aryl pyrrole.

20. Method as in claim 2 in which said compound is

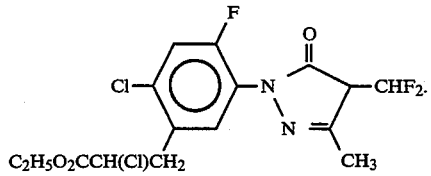

21. Method as in claim 2 in which said compound is

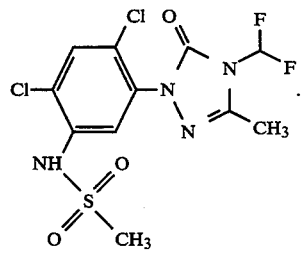

* * * * *